United States Patent
Golinski

(10) Patent No.: US 6,447,552 B1
(45) Date of Patent: Sep. 10, 2002

(54) PROCESS FOR THE PREPARATION OF STABLE AQUEOUS HAIR DYEING EMULSIONS

(75) Inventor: Frank Golinski, Darmstadt (DE)

(73) Assignee: Goldwell GmbH (DE)

( * ) Notice: Subject to any disclaimer, the term of this patent is extended or adjusted under 35 U.S.C. 154(b) by 0 days.

(21) Appl. No.: 09/272,919

(22) Filed: Mar. 19, 1999

(30) Foreign Application Priority Data

Apr. 6, 1998 (DE) .......................................... 198 15 338

(51) Int. Cl.[7] .............................. A61K 7/13; A61K 7/06
(52) U.S. Cl. ....................... 8/406; 8/435; 8/580; 8/649; 8/902
(58) Field of Search ............................ 8/406, 435, 580, 8/649, 902

(56) References Cited

U.S. PATENT DOCUMENTS

| | | | | |
|---|---|---|---|---|
| 4,381,920 A | * | 5/1983 | Garlen ........................... | 8/406 |
| 5,651,793 A | * | 7/1997 | Hoeffkes et al. ................ | 8/406 |
| 5,656,280 A | * | 8/1997 | Herb et al. ..................... | 8/406 |
| 5,817,155 A | * | 10/1998 | Yasuda et al. .................. | 8/406 |

FOREIGN PATENT DOCUMENTS

| | | |
|---|---|---|
| DE | 4017718 | 12/1991 |
| JP | 9-249537 | * 9/1997 |

OTHER PUBLICATIONS

CAPLUS Abstract of WO9851267, Henkel, Nov. 1998.*

CAPLUS Abstract, "Study on the Stability of Hair Dyeing Cream," Xu et al, Riyong Huaxue Gongye, 1997 (No month available).*

English language translation of JP 9–249,537, Shiseido Co., Ltd., pp. 1–32, Sep. 1997.*

* cited by examiner

Primary Examiner—John Hardee
Assistant Examiner—Brian P. Mruk
(74) Attorney, Agent, or Firm—Norris, McLaughlin & Marcus P.A.

(57) ABSTRACT

A simplified process is presented for the preparation of stable, aqueous hair dyeing emulsions, comprising at least one oxidation hair dyestuff precursor, by first preparing a homogenous oily phase comprising at least one oil-soluble emulsifier by mixing the oil components at an increased temperature between 40° and 80° C., and subsequently mixing this oily phase with an aqueous phase, comprising at least one water-soluble emulsifier under shearing force at a temperature between 15° and 30° C. Compared to conventional processes of hot emulsification, this process substantially reduces the preparation time.

5 Claims, No Drawings

PROCESS FOR THE PREPARATION OF STABLE AQUEOUS HAIR DYEING EMULSIONS

BACKGROUND OF THE INVENTION

The present invention concerns an improved process for the preparation of stable, aqueous hair dyeing emulsions.

Permanent hair dyeing emulsions customarily comprising at least one oxidation dyestuff precursor, namely a developer-coupler system, are generally used in form of aqueous emulsions (see K. Schrader, "Grundlagen und Rezepturen der Kosmetika", 2nd Ed. (1989), pp. 797 ff).

The preparation thereof takes place by hot emulsification of the components and subsequent cooling, which, of course, needs a substantial period of time without always leading to stable emulsions.

SUMMARY OF THE INVENTION

There was, therefore, the need to modify and simultaneously optimize the current manufacturing process.

It has now been found that a stable, aqueous hair dyeing emulsion comprising at least one oxidation hair dyestuff precursor with good Theological properties can be obtained, while simultaneously substantially reducing the manufacturing time and respective energy consumption, by first preparing a homogenous oily phase by mixing the oil components with at least one oil-soluble emulsifier at 40° to 80°, preferably 45° to 70° C., and subsequently mixing this oily phase with an aqueous phase comprising at least one water-soluble emulsifier under shearing force, i.e. stirring, at 15° to 30° C., i.e. preferably at room temperature at about 20° to 25° C.

The finished product thus obtained preferably has a viscosity ranging from 2,500 to 25,000, in particular between 5,000 and 25,000, preferably 20,000, especially preferred from 12,000 to 18,000 mPa.s, measured at 20° C. in the Brookfield-Viscosimeter RVT.

The proportion of the oily phase in the total emulsion preferably ranges from about 10% to about 40%, especially 15% to 30% by weight, calculated to the total emulsion.

The oil bodies incorporated in the oily phase are customary cosmetic oils and fats, for example natural oils such as avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or also olive oil, soya oil, lanolin and the derivatives thereof, as well as mineral oils such as paraffin oil and petrolatum.

Synthetic oils and waxes are, for example, silicone oils, polyethyleneglycols, etc. Further suitable hydrophobic components are in particular fatty alcohols, preferably those with about 8 to 22 carbon atoms in the molecule, such as myristyl, cetyl, stearyl alcohol, wax alcohols and fatty acid esters such as isopropyl myristate, palmitate, stearate and isostearate, oleyl oleate, isocetyl stearate, hexyl laurate, dibutyl adipate, dioctyl adipate, myristyl-myristate, oleyl erucate, polyethyleneglycol and polyglyceryl fatty acid esters such as PEG-7-glyceryl cocoate, cetyl palmitate, etc.

Depending on the character and type of the oil-soluble emulsifiers, their proportion in the oil phase preferably amounts about 50% to 95%, in particular about 60% to 90% by weight.

Suitable oil-soluble emulsifiers are in particular those of the nonionic type, such as the various fatty alcohol ethoxylates, such as lauryl, myristyl, cetyl, oleyl, tridecyl, isotridecyl, coco fatty and tallow fatty alcohol ethoxylates, etc.; however, it is also possible to use further nonionic oil-soluble emulsifiers known per se. Their proportion in the oily phase is variable and can range between about 5% and about 50%, in particular about 10% to about 40% by weight, calculated to the total oily phase.

Useful as water-soluble emulsifiers in the water phase are in particular anionic surfactants. Suitable anionic surfactants within the scope of the invention are contained in an amount from about 0.25% to about 5% by weight, preferably about 0.4% to 2.5% by weight, calculated to the total (ready-to-use) composition.

These are surfactants of the sulfate, sulfonate, carboxylate and alkyl phosphate type, especially, of course, those customarily used in hair treatment compositions, in particular the known $C_{10}$–C–$C_{18}$-alkyl sulfates, and particularly the respective ether sulfates, for example, $C_{12}$–$C_{14}$-alkyl ether sulfate, lauryl ether sulfate, especially with 1 to 4 ethylene oxide groups in the molecule, the known $C_{10}$–$C_{18}$-alkyl sulfates and the respective ether sulfates, acylamino carboxylic acids such as lauroyl sarcosinate and glutamate, furthermore monoglyceride(ether) sulfates, fatty acid amide sulfates, obtained by ethoxylation and subsequent sulfatation of fatty acid alkanolamides, and the alkali salts thereof, as well as the salts of long-chain mono-and dialkyl phosphates, which are mild, skin-compatible detergents.

Further anionic surfactants useful within the scope of the invention are α-olefin sulfonates or the salts thereof, and in particular alkali salts of sulfosuccinic acid semiesters, for example the disodium salt of monooctyl sulfosuccinate and alkali salts of long-chain monoalkyl ethoxysulfosuccinates.

Useful surfactants of the carboxylate type are alkyl polyether carboxylic acids and the salts thereof of the formula

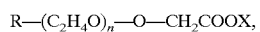

wherein R is a $C_8$–$C_{20}$-alkyl group, preferably a $C_{12}$–$C_{14}$-alkyl group, n is a number from 1 to 20, preferably 2 to 17, and X is H or preferably a cation of the group sodium, potassium, magnesium and ammonium, which may optionally be hydroxyalkyl-substituted, as well as alkyl amido polyether carboxylic acids of the general formula

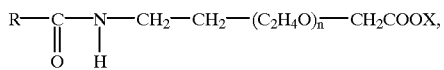

wherein R and X have the above meanings and n is in particular a number from 1 to 10, preferably 2.5 to 5.

Such products have been known and have been on the market for some time, for example under the trade name "AKYPO" and "AKYPO-SOFT®".

$C_8$–$C_{20}$-acylisethionates can also be used alone or in admixture with other surfactants, as well as sulfofatty acids and the esters thereof.

It is optionally also possible to use amphoteric or zwitterionic surfactants as water-soluble emulsifiers, in particular in admixture with anionic surfactants, whereby the total amount should preferably range from about 0.25% to 5% by weight, calculated to the total hair dyeing composition.

Useful as such are in particular the various known betaines such as fatty acid amido alkyl betaines and sulfobetaines, for example, lauryl hydroxy sulfobetaine, also long-chain alkyl-amino acids such as cocoaminoacetate, cocoaminopropionate and sodium cocoamphopropionate and-acetate.

In detail, it is possible to use betaines of the structure

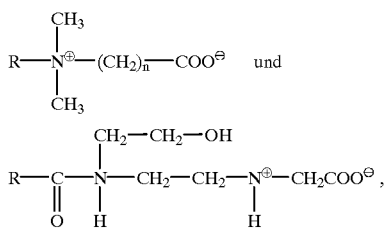

wherein R is a $C_8$–$C_{18}$-alkyl group and n is 1 to 3, sulfobetaines of the structure

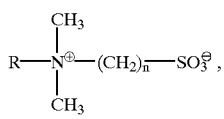

wherein R is a $C_8$–$C_{18}$-alkyl group and n is 1 to 3, and amido alkylbetaines of the structure

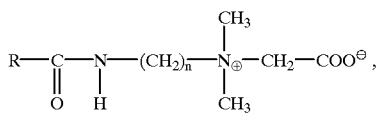

wherein R is a $C_8$–$C_{18}$-alkyl group and n is 1 to 3.

Also possible is the use of nonionic water-soluble surfactants, e.g., of $C_8$–$C_{18}$-alkyl polyglucosides with a polymerization degree of 1 to 5 alone in the amounts named above, or in admixture with anionic and/or amphoteric or zwitterionic surface-active substances.

Further useful nonionic substances are amineoxides and fatty acid mono-and-dialkanol amides.

Further suitable surfactants are also cationic surfactants such as the known quaternary ammonium compounds with one or two alkyl or alkenyl groups with 10 to 22 carbon atoms in the molecule, in particular in an amount ranging from 0.1% to 7.5%, preferably 0.25% to 5%, especially preferred 0.5% to 2.5% by weight, calculated to the total composition.

Suitable long-chain quaternary ammonium compounds which can be used alone or in admixture are in particular cetyl trimethyl ammonium chloride, dimethyl dicetyl ammonium chloride, trimethyl cetyl ammonium bromide, behenyl trimonium chloride, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, lauryl trimethyl ammonium chloride, tris-(oligooxyethyl) alkyl ammonium phosphate, cetyl pyridinium chloride, etc. It is basically possible to use all quaternary ammonium compounds listed under the generic name "Quaternium" in the CTFA International Cosmetic Ingredient Dictionary.

The hair dyeing emulsion prepared according to the invention comprises at least one oxidation dyestuff precursor, preferably a mixture of at least one developing and at least one coupling substance.

These are known per se and described, for example, in the monography of K. Schrader, "Grundlagen und Rezepturen der Kosmetika", 2nd Ed. (1989), pp. 784–799.

Examples of developing substances are in particular 1.4-diaminobenzene, 2.5-diaminotoluene, tetraaminopyrimidines, triaminohydroxypyrimidines, 1.2.4-triaminobenzene, 2-(2.5-diaminophenyl)ethanol, 2-(2'-hydroxyethyl amino)-5-aminotoluene and 1-amino-4-bis-(2'-hydroxyethyl)-aminobenzene, or the water-soluble salts thereof; examples for coupling substances are resorcinol, 2-methyl resorcinol, 4-chlororesorcinol, 2-amino-4-chlorophenol, 4-(N-methyl) aminophenol, 2-arninophenol, 3-aminophenol, 1-methyl-2-hydroxy-4-aminobenzene, 3-N, N-dimethyl aminophenol, 4-amino-3-methyl phenol, 5-amino-2-methyl phenol, 6-amino-3-methyl phenol, 3-amino-2-methyl amino-6-methoxypyridine, 2-amino-3-hydroxypyridine, 4-aminodiphenylamine, 4.4'-diaminodiphenyl-amine, 2-dimethyl amino-5-aminopyridine, 2.6-diaminopyridine, 1.3-diaminobenzene, 1-amino-3-(2'-hydroxyethyl amino)benzene, 1-amino-3-[bis(2'-hydroxyethyl) amino]benzene, 1,3-diamino-toluene, α-naphthol, 1.4-diamino-2-chlorobenzene, 4.6-dichlororesorcinol, 4-hydroxy-1.2-methylene dioxybenzene, 1.5-dihydroxynaphthaline, 1.7-dihydroxynaphthaline, 2.7-dihydroxynaphthaline, 1-hydroxynaphthaline, 2.4-diamino-3-chlorophenol, and/or 1-methoxy-2-amino-4-(2'-hydroxyethyl amino) benzene, whereby this list of examples is not complete.

Developing and coupling substances are preferably contained in a molar proportion of 1:3 to 5:1, in particular about 1:1 and about 3:1; their proportion in the hair dyeing compositions according to the invention may range from about 0.1% to about 5% by weight, depending on the desired coloration.

These oxidation dyestuff precursors are preferably already contained in the aqueous phase; however, when desired they can also be added to the finished product simultaneously with the oily phase or subsequently thereto.

The compositions according to the invention may also comprise so-called shading agents for the fine adjustment of the desired color, in particular also direct-acting dyestuffs.

Such shading agents are, for example, nitro-dyestuffs such as 2-amino-4.6-dinitrophenol, 2-amino-4-nitrophenol, 2-amino-6-chloro-4-nitrophenol, etc., preferably in amounts from about 0.05% to 2.5%, in particular 0.1% to 1% by weight, calculated to the total dyestuff composition (excluding the oxidation agent).

The hair dyeing compositions prepared according to the invention can also comprise the basic substances and additives customarily found in such compositions, i.e. conditioners, stabilizers, thickening agents, complexing agents, etc. known as state of the art and described, for example, in the monography of K. Schrader, "Grundlagen und Rezepturen der Kosmetika", 2nd Ed. (Hüithig Buch Verlag, Heidelberg, 1989), pp. 782 to 815.

The hair dyeing emulsions prepared according to the invention preferably have a pH-value in the alkaline range, especially between about 8 and about 12.5, in particular between 8.5 and 11.

For application, the oxidation dyestuff precursor prepared according to the invention is mixed with an oxidation agent. The preferred oxidation agent is hydrogen peroxide, for example in a concentration of 2% to 6%.

It is also possible, however, to use other peroxides such as urea peroxide and melamine peroxide.

The pH-value of the ready-to-use hair dyeing composition, i.e. after admixture with peroxide, may be slightly acidic, i.e. ranging between 5.5 to 6.9, as well as neutral or alkaline, i.e. ranging between pH 7.1 and 10.

DESCRIPTION OF THE PREFERRED EMBODIMENTS

The following two Examples illustrate the invention.

EXAMPLE 1

22.5 g cetyl stearyl alcohol, 67.5 g paraffin oil and 10 g Oleth-5 are melted at 50° C. under constant stirring, and subsequently cooled down to room temperature (20° C.). A homogenous paste is obtained (oily phase).

Into 80 g of a solution comprising

| | |
|---|---|
| 0.5 g | sodium lauryl sulfate, |
| 0.1 g | ascorbic acid, |
| 0.5 g | ammonium chloride, |
| 0.2 g | sodium sulfite, |
| 0.2 g | tetrasodium-EDTA, |
| 10.0 g | 25% ammonia, |
| 0.9 g | wheat protein hydrolyzate, |
| 0.6 g | panthenol, |
| 0.5 g | hop extract, |
| 0.4 g | perfume oil, |
| 0.55 g | p-toluylenediamine sulfate, |
| 0.05 g | resorcinol, |
| 0.02 g | 4-chlororesorcinol, |
| 0.02 g | 3-aminophenol, and |
| ad 80.00 g | water | were added 20 g of the oily phase at 25° C. in an Ultraturrax at 9,500 r/pm and stirred for 1 to 2 minutes.

The product had a viscosity of about 15 000 mPa.s, measured in the Brookfield-Viscosimeter RVT at 20° C.

After mixing with a 6% $H_2O_2$-solution in a ratio of 1:1, a stable coloring emulsion was obtained, which resulted in a medium blond coloration after application to human hair.

EXAMPLE 2

169 g oleyl alcohol, 56 g cetyl stearyl alcohol and 25 g leth-5 were melted together at 60° C. and subsequently cooled down to about 25° C.

Under stirring for about 3 minutes at about 20° C. (at about 10,000 r/pm), 25 g of the pasty oily phase thus obtained were added to 75 g of a water phase of the following composition:

| | |
|---|---|
| 0.50 g | sodium lauryl sulfate, |
| 0.25 g | cocoamidopropyl betaine, |
| 0.05 g | tetrasodium-EDTA, |
| 0.60 g | panthenol, |
| 0.50 g | ammonium chloride, |
| 1.00 g | sodium sulfite, |
| 1.00 g | wheat protein hydrolyzate, |
| 0.50 g | horse chestnut extract, |
| 0.50 g | ascorbic acid, |
| 0.40 g | perfume, |
| 0.40 g | p-toluylenediamine sulfate, |
| 0.05 g | resorcinol, |
| 0.10 g | 3-aminophenol, |
| 0.25 g | 4-aminophenol, |
| 0.05 g | p-amino-o-cresol, |
| ad 75.00 g | water. |

A stable hair dyeing emulsion was obtained with a viscosity of about 17,000 mPa.s at 20° C. (Brookfield-Viscosimeter RVT), which resulted in a glossy red-brown hair coloration on human hair according to the dyeing method described in Example 1.

Preparation of a hair dyeing emulsion according to the conventional method of hot emulsification of all components required a period of time exceeding by far that of the method described above.

A further major advantage of the process according to the invention is that the oily phase can be prepared in larger quantities and kept in storage for the cold preparation of hair dyeing emulsions.

What is claimed is:

1. Process for the preparation of stable aqueous hair dyeing emulsions comprising at least one oxidation dyestuff precursor, comprising the steps of:

(a) first preparing a homogenous oily phase from oil components comprising at least one oil-soluble emulsifier and an oil, by mixing the oil components at a temperature between 40° and 80° C., (b) cooling the oily phase to a temperature between about 15° and 30° C.

(c) subsequently mixing the oily phase with an aqueous phase comprising at least one water-soluble emulsifier, under shearing force, at a temperature between 15° and 30° C., and wherein the emulsion contains at least one oxidation dyestuff precursor.

2. Process according to claim 1, wherein the oily phase is prepared at a temperature ranging from 45° to 70° C.

3. Process according to claim 1, wherein the stable aqueous hair dyeing emulsion has a viscosity between 2,500 and 25,000 mPa.s at 20° C. in a Brookfield-Viscometer RVT.

4. Process according to claim 3, wherein the hair dyeing emulsion has a viscosity between 5,000 and 20,000 mPa.s at 20° C. in a Brookfield-Viscometer RVT.

5. The method of claim 1, wherein step (c) consists of mixing for about 1–3 minutes.

* * * * *